(12) United States Patent
Kim et al.

(10) Patent No.: US 11,707,545 B2
(45) Date of Patent: *Jul. 25, 2023

(54) LIGHT SOURCE MODULE AND ULTRAVIOLET RAY IRRADIATING APPARATUS INCLUDING THE SAME

(71) Applicant: SUZHOU LEKIN SEMICONDUCTOR CO., LTD., Taicang (CN)

(72) Inventors: Dae Hun Kim, Seoul (KR); Ki Hyun Kim, Seoul (KR); Sang Hun An, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/682,958

(22) Filed: Feb. 28, 2022

(65) Prior Publication Data

US 2022/0175991 A1 Jun. 9, 2022

Related U.S. Application Data

(63) Continuation of application No. 16/971,257, filed as application No. PCT/KR2019/002059 on Feb. 20, 2019, now Pat. No. 11,305,028.

(30) Foreign Application Priority Data

Feb. 20, 2018 (KR) ........................ 10-2018-0020050

(51) Int. Cl.
*A61L 2/10* (2006.01)
*A61L 2/04* (2006.01)
*B66B 31/02* (2006.01)

(52) U.S. Cl.
CPC ................... *A61L 2/10* (2013.01); *A61L 2/04* (2013.01); *B66B 31/02* (2013.01); *A61L 2202/11* (2013.01)

(58) Field of Classification Search
CPC .......... A61L 2/10; A61L 2/04; A61L 2202/11; B66B 31/02

(Continued)

(56) References Cited

U.S. PATENT DOCUMENTS

| 7,338,181 B2 | 3/2008 | Yuen |
| 11,305,028 B2 * | 4/2022 | Kim .......................... A61L 2/10 |

(Continued)

FOREIGN PATENT DOCUMENTS

| CN | 203159026 U | 8/2013 |
| EP | 3272692 A1 | 1/2018 |

(Continued)

*Primary Examiner* — Nicole M Ippolito
(74) *Attorney, Agent, or Firm* — Birch, Stewart, Kolasch & Birch, LLP

(57) ABSTRACT

A light source module including a fixing plate configured to extend in a first direction; a circuit board disposed on the fixing plate; a plurality of ultraviolet light emitting elements disposed on the circuit board in the first direction; a first reflection plate disposed at one side of the fixing plate; and a second reflection plate disposed at the other side of the fixing plate. Further, the plurality of ultraviolet light emitting elements are disposed between the first reflection plate and the second reflection plate in the first direction.

20 Claims, 17 Drawing Sheets

(58) Field of Classification Search
USPC .............. 250/453.11, 454.11, 455.11, 504 R
See application file for complete search history.

(56) References Cited

U.S. PATENT DOCUMENTS

| | | |
|---|---|---|
| 2005/0217971 A1 | 10/2005 | Kim |
| 2008/0185605 A1 | 8/2008 | Wada et al. |
| 2011/0158862 A1 | 6/2011 | Kim et al. |
| 2015/0028228 A1 | 1/2015 | Almasy et al. |
| 2018/0099842 A1 | 4/2018 | Kim et al. |
| 2019/0267357 A1 | 8/2019 | Iguchi et al. |

FOREIGN PATENT DOCUMENTS

| | | |
|---|---|---|
| JP | 2005-200211 A | 7/2005 |
| JP | 2006-193319 A | 7/2006 |
| KR | 10-2006-0105239 A | 10/2006 |
| KR | 10-2011-0066476 A | 6/2011 |
| KR | 10-2013-0124026 A | 11/2013 |
| KR | 10-1415154 B1 | 7/2014 |
| KR | 10-2016-0112422 A | 9/2016 |

\* cited by examiner

[FIG. 1]
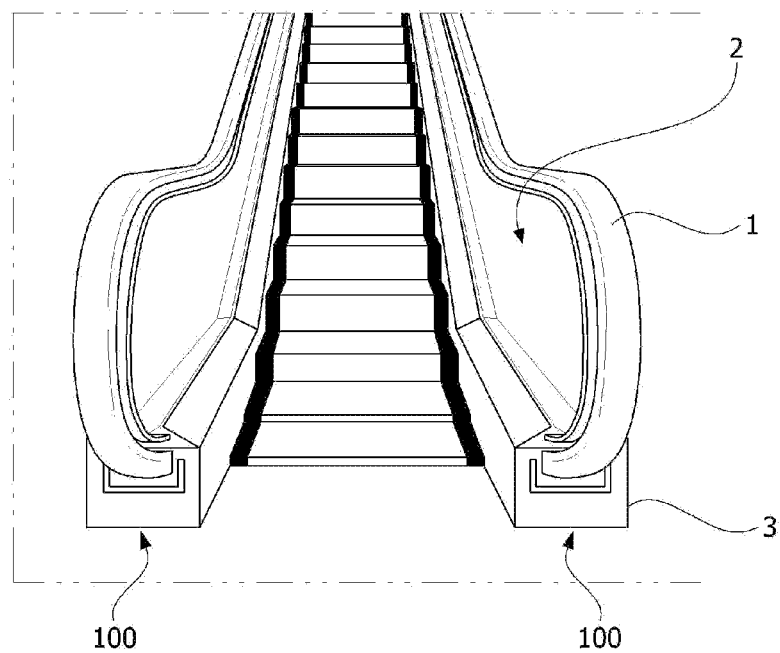

[FIG. 2]
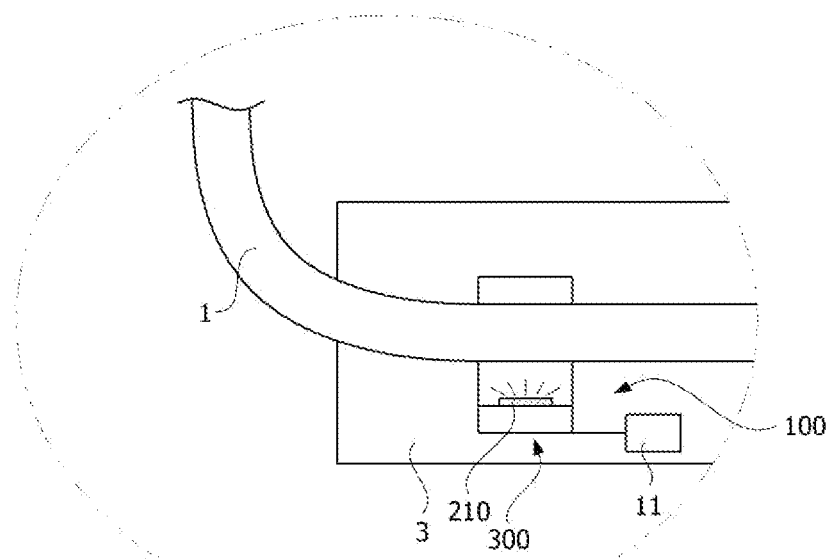
[FIG. 3a]
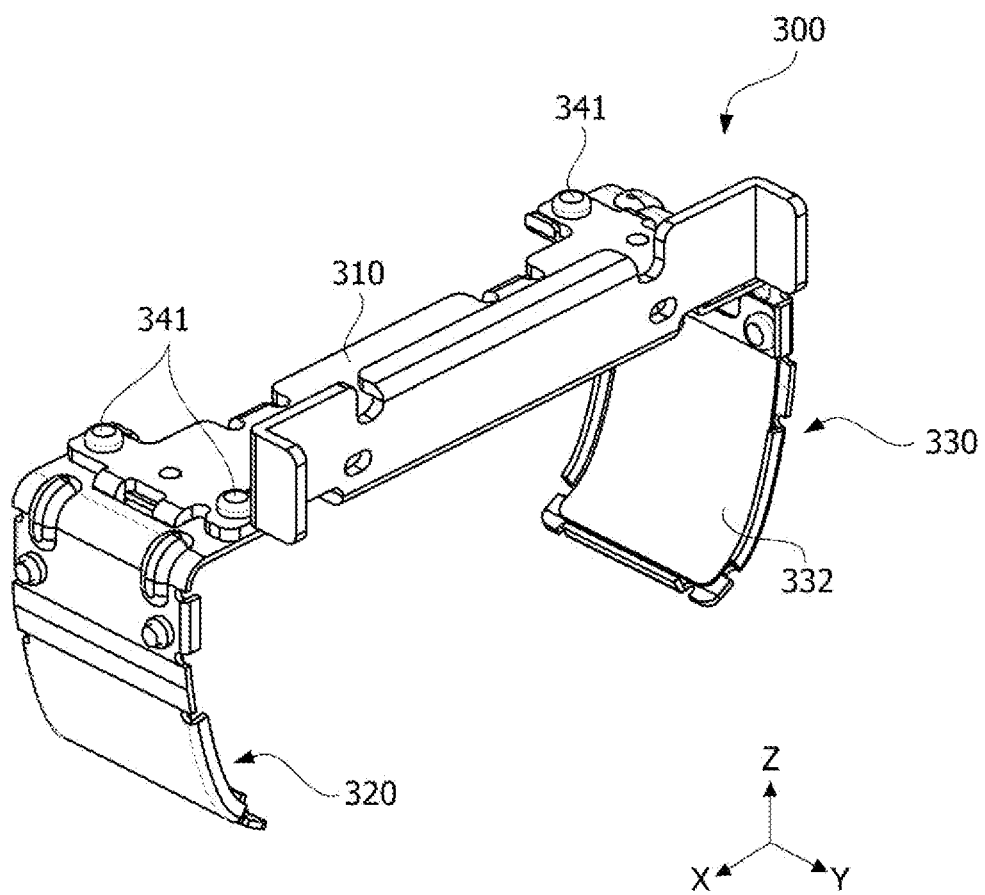

[FIG. 3b]
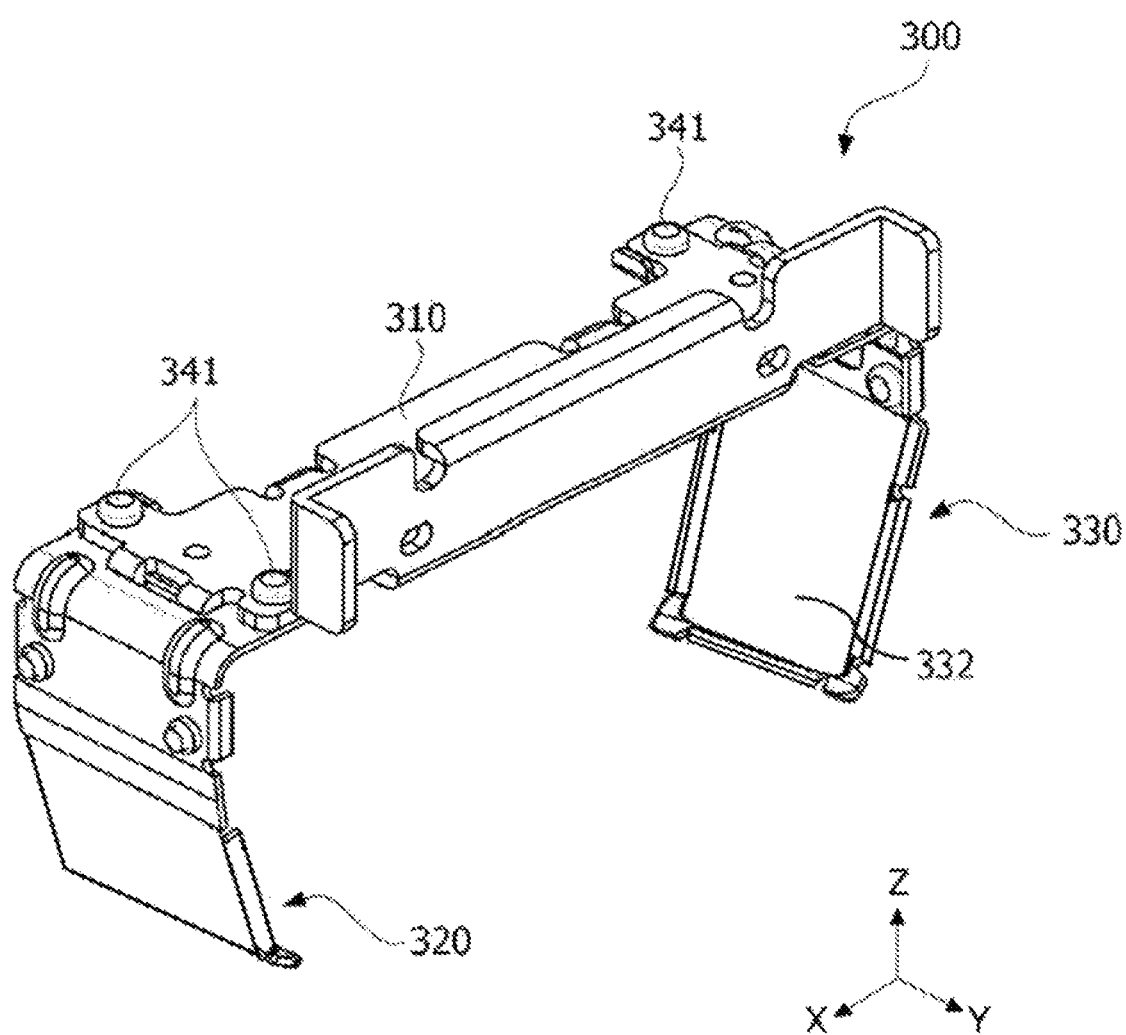

[FIG. 4]
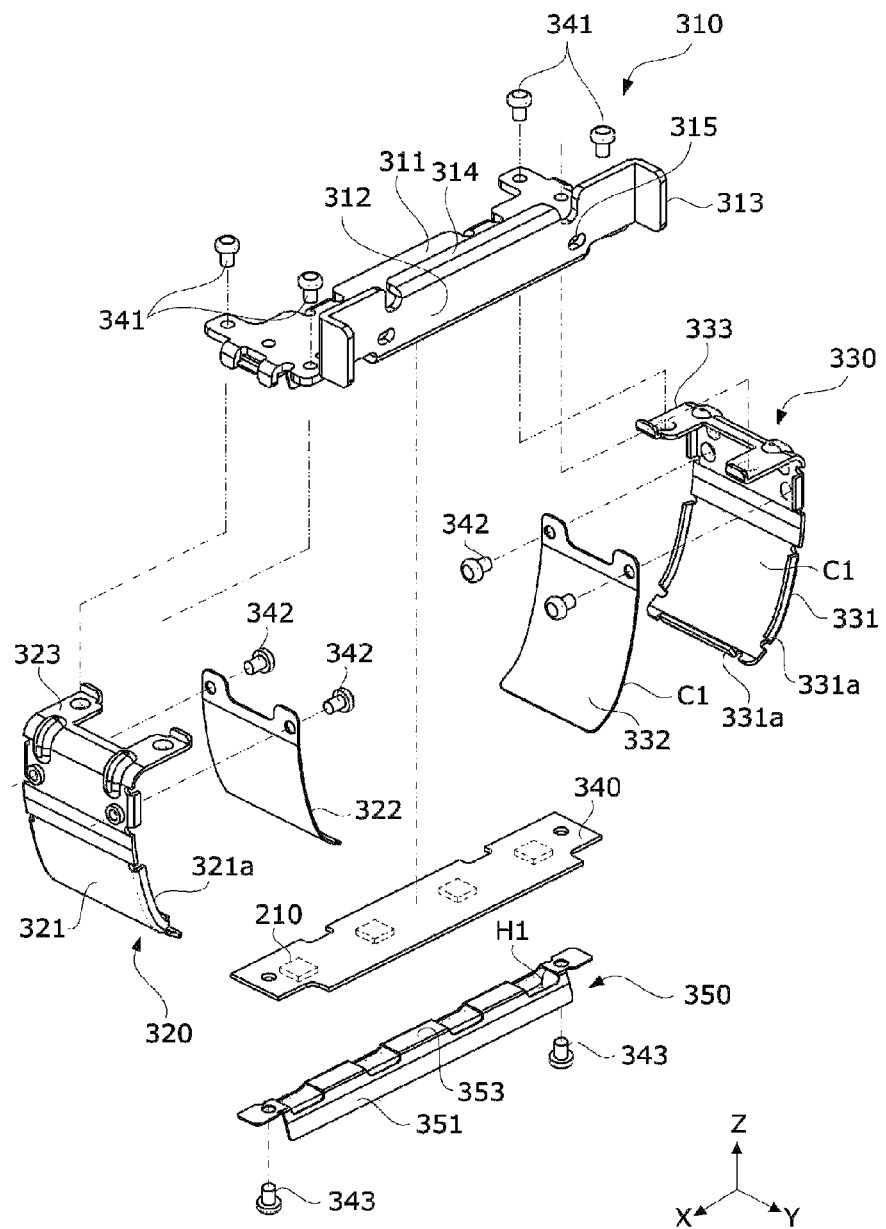

[FIG. 5]
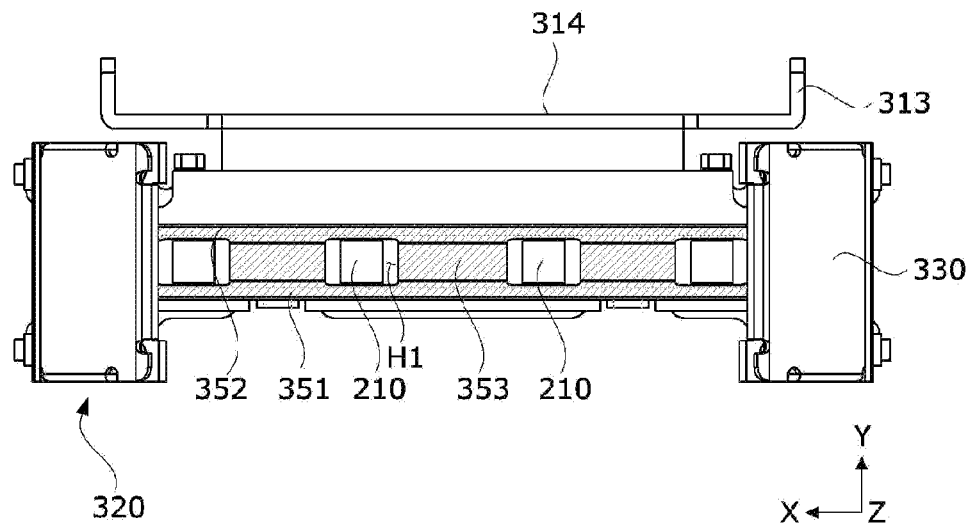
[FIG. 6]
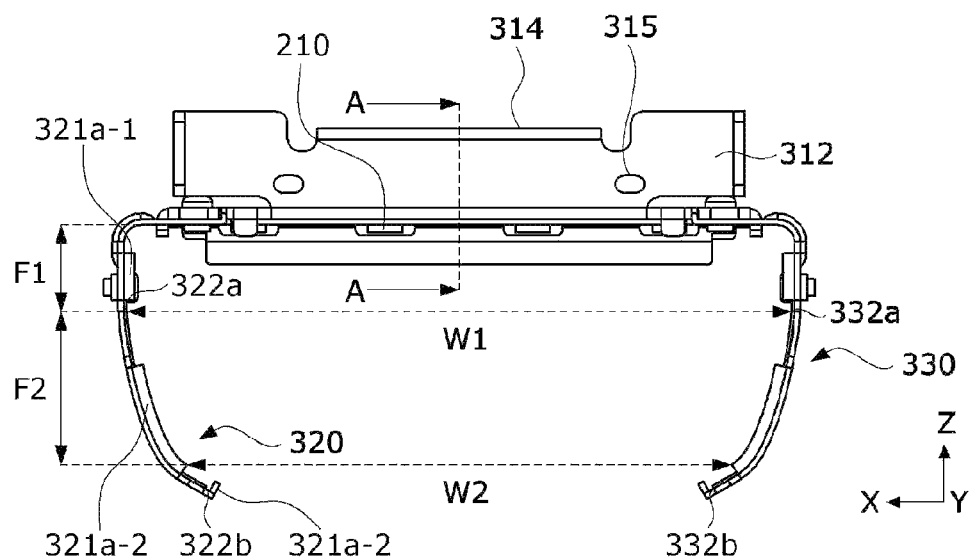

[FIG. 7]
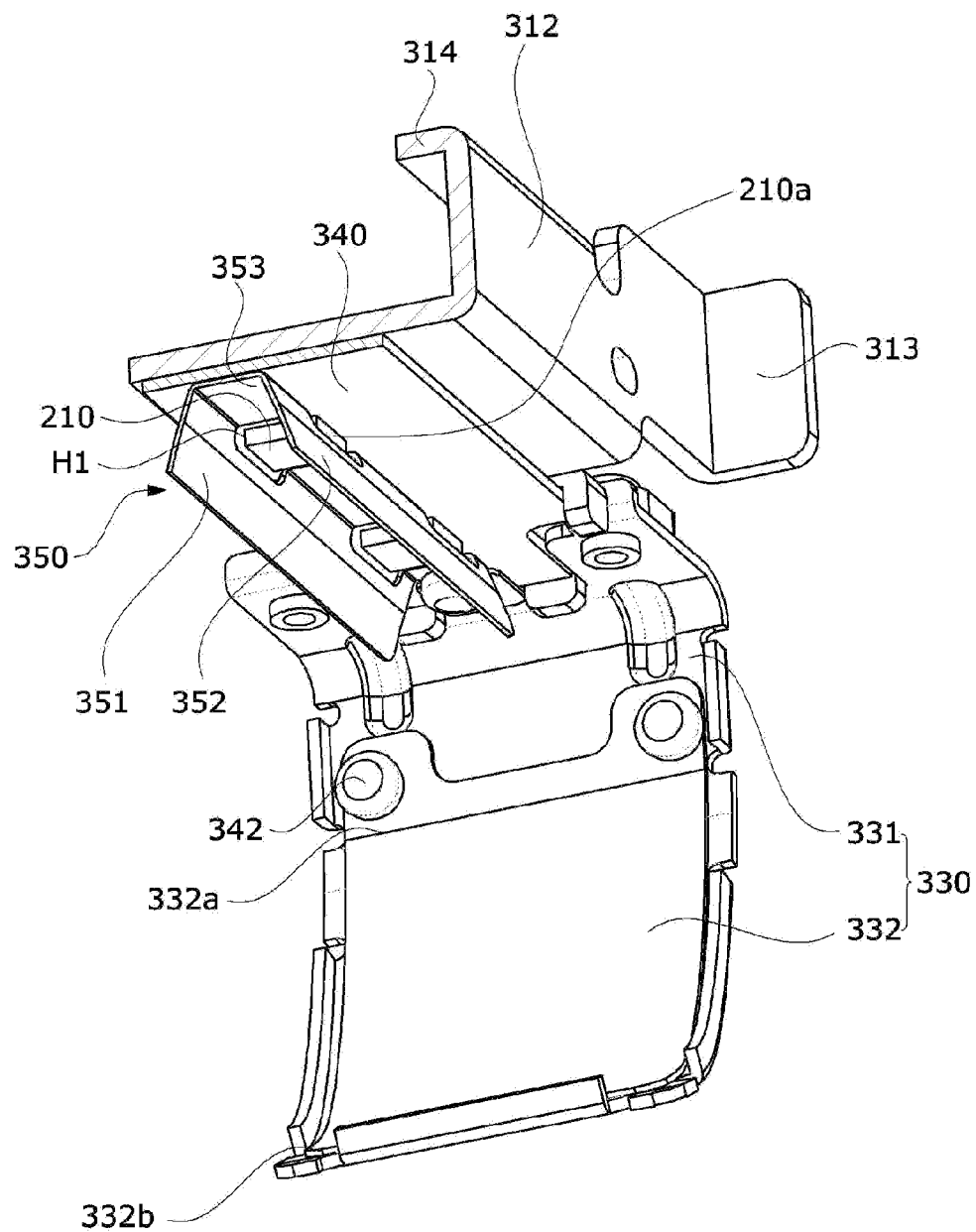

[FIG. 8]
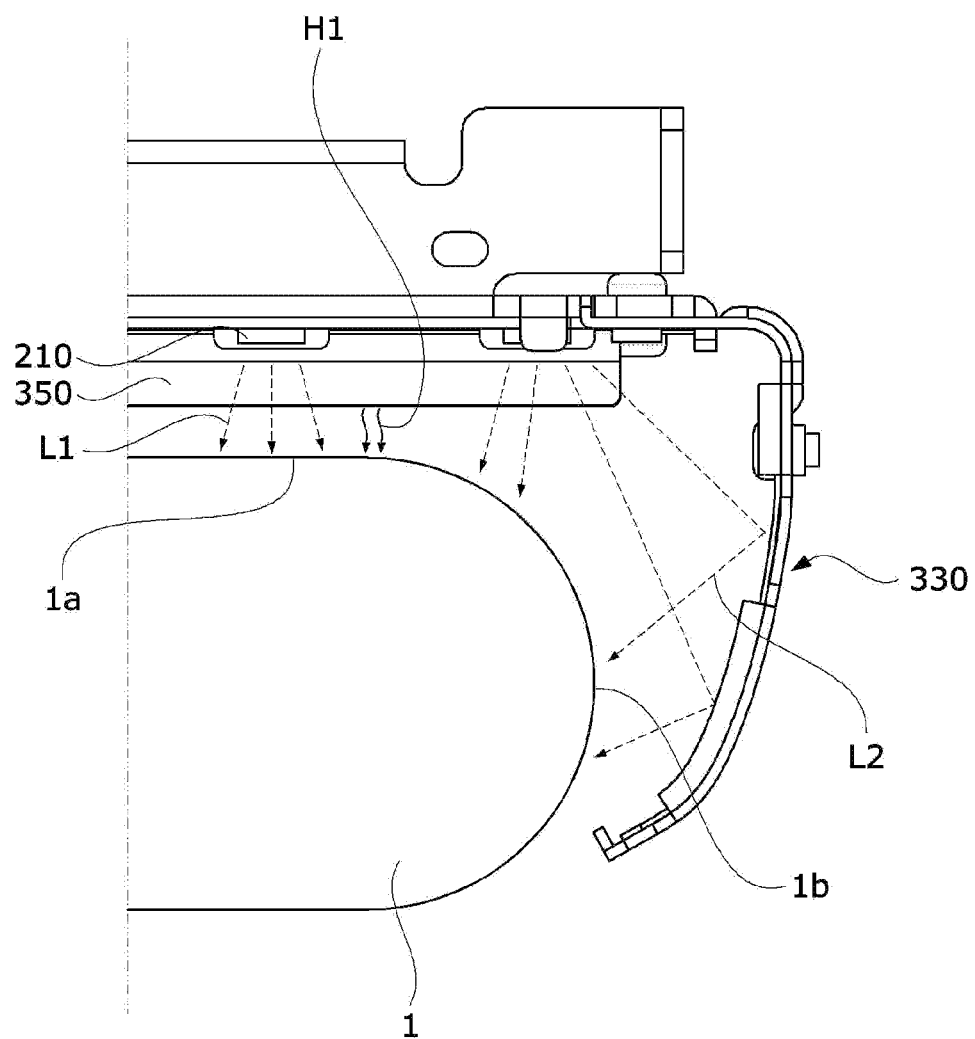

[FIG. 9a]
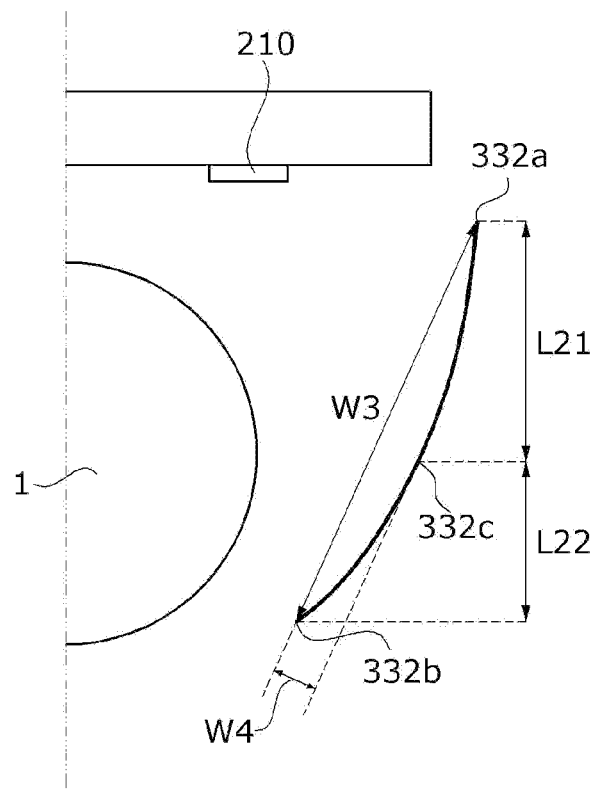
[FIG. 9b]
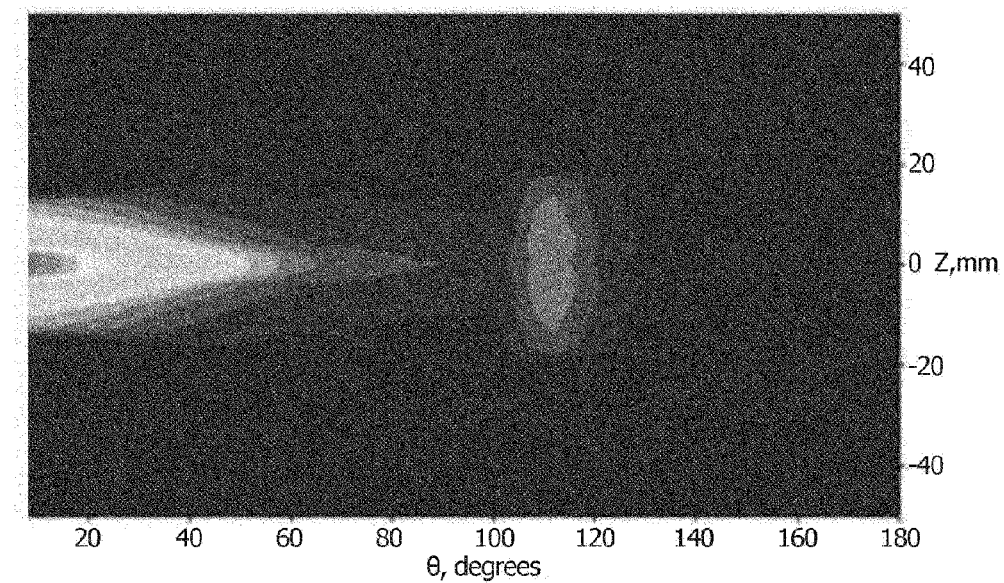

[FIG. 10a]
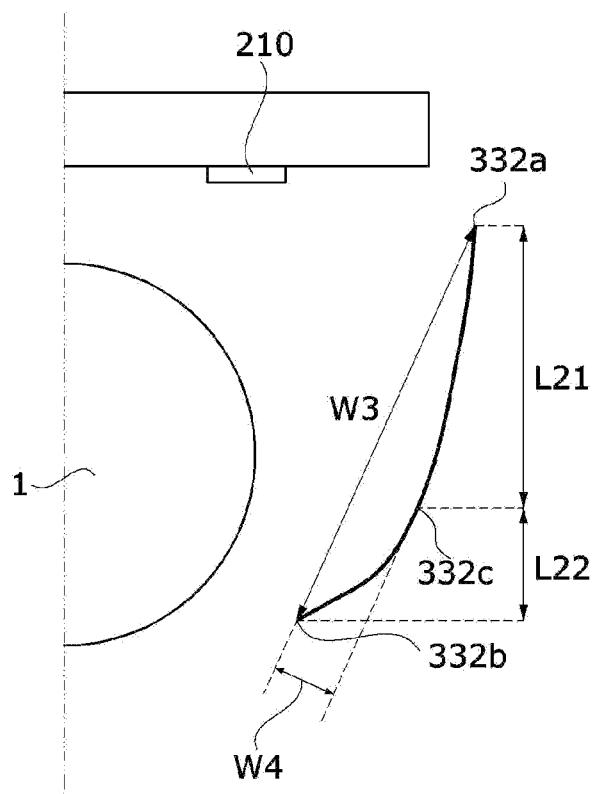

【FIG. 10b】
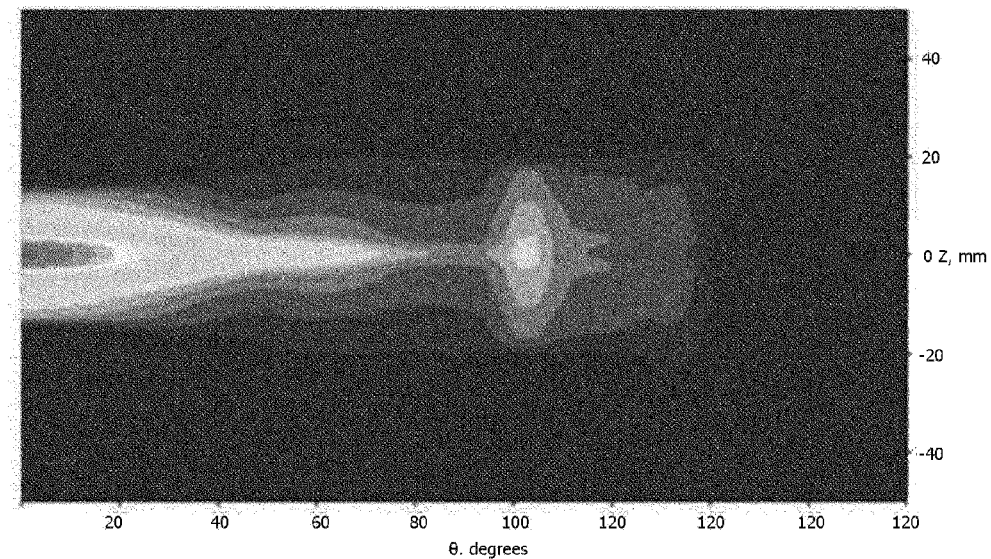
【FIG. 11a】
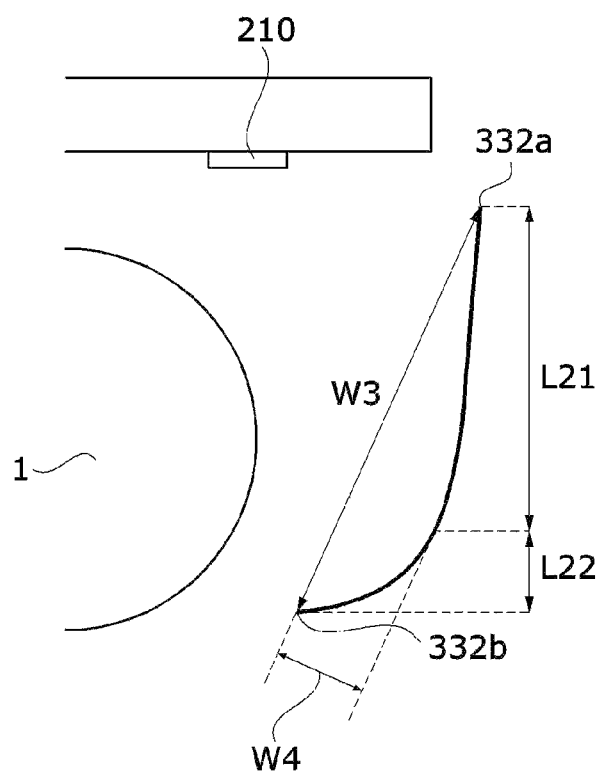

[FIG. 11b]
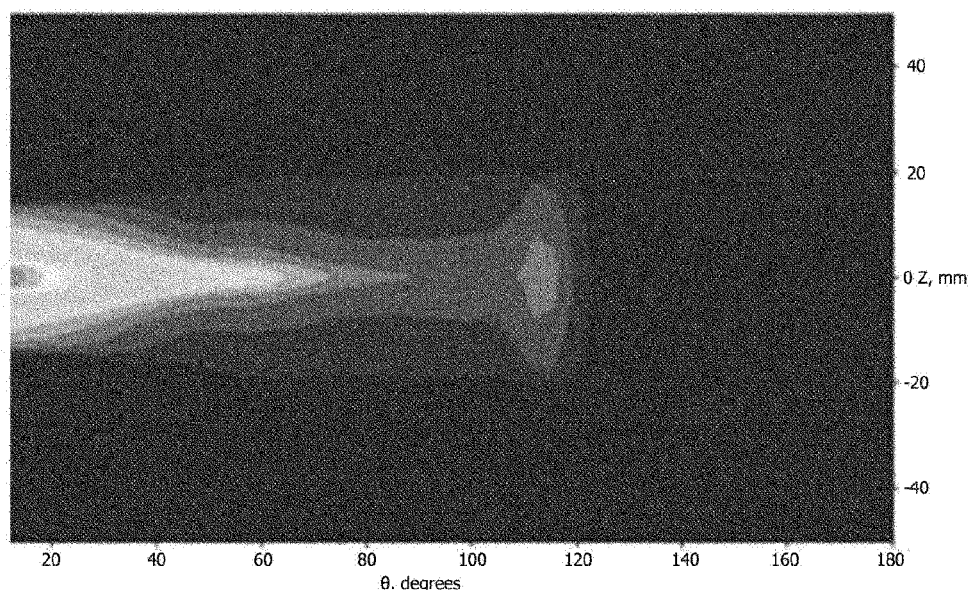

[FIG. 12a]
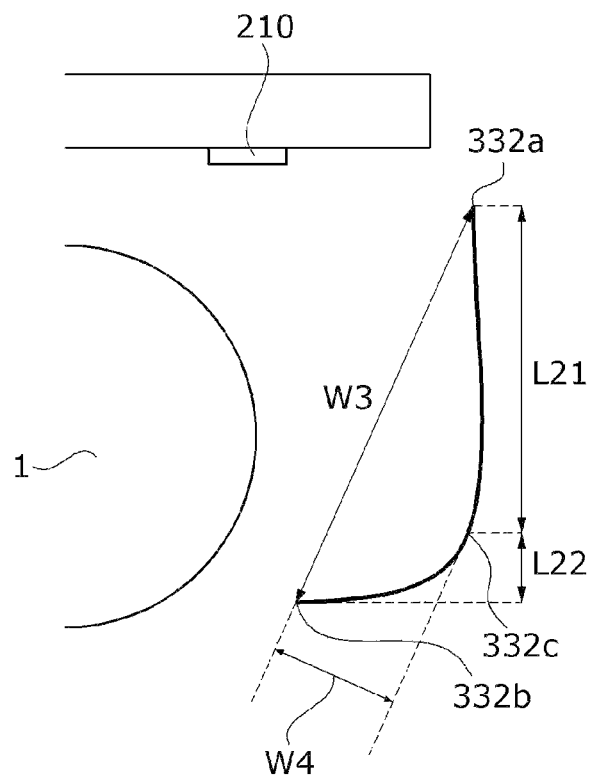
[FIG. 12b]
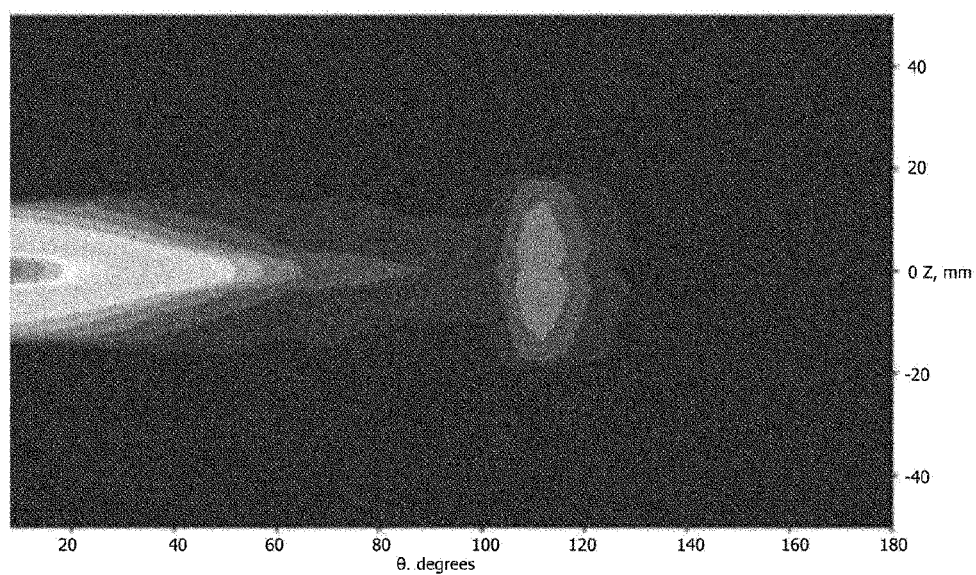

[FIG. 13]
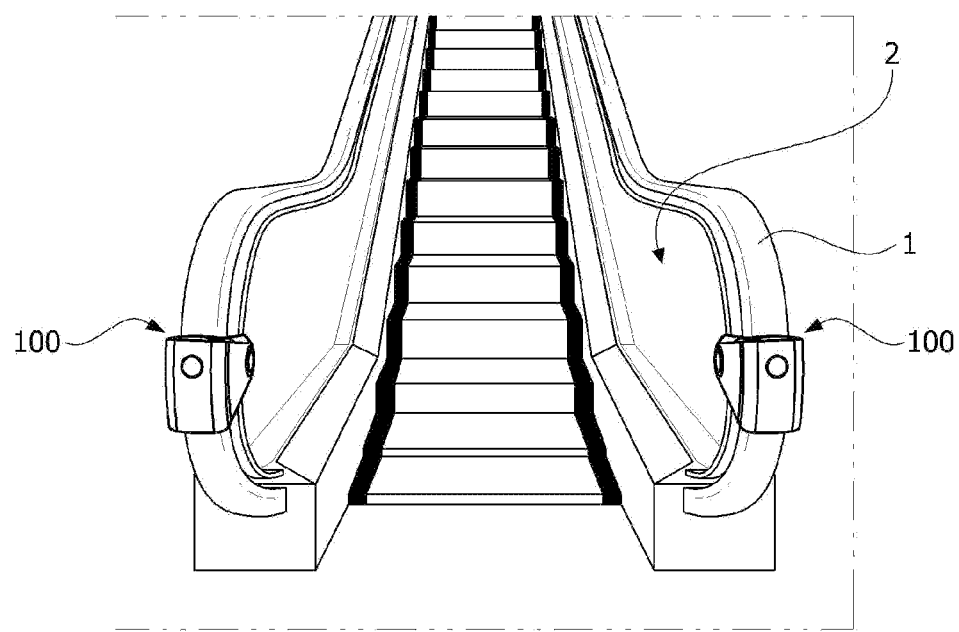

[FIG. 14]
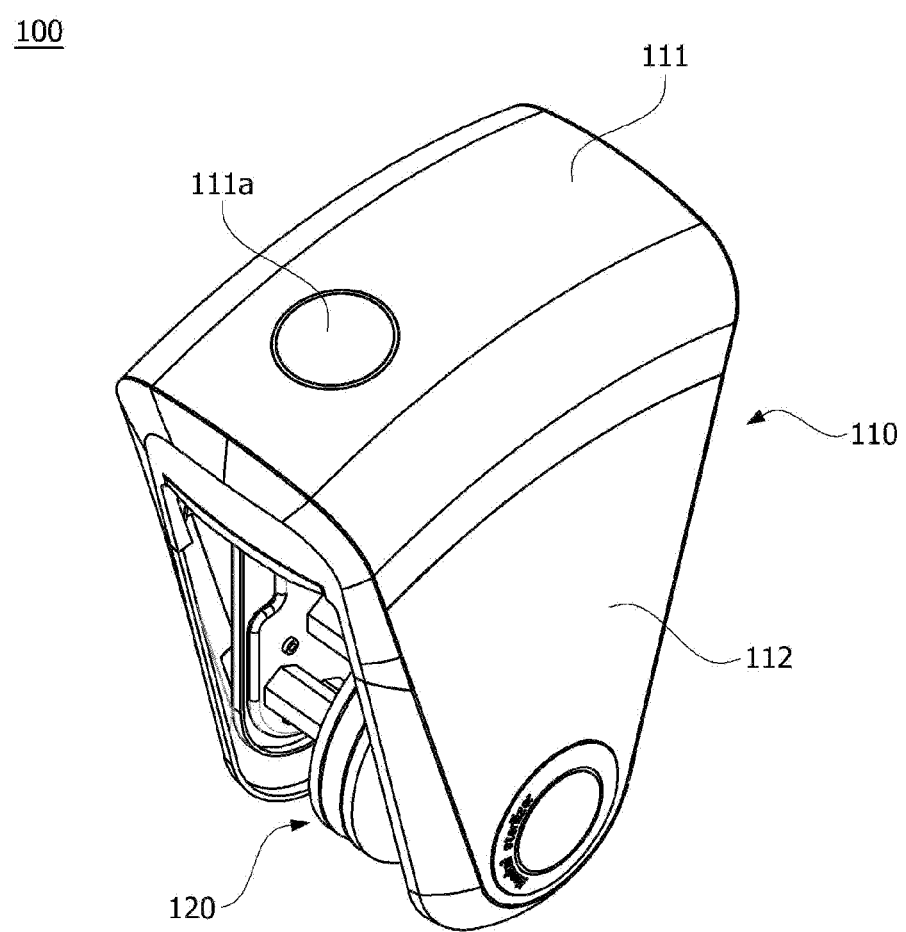

[FIG. 15]
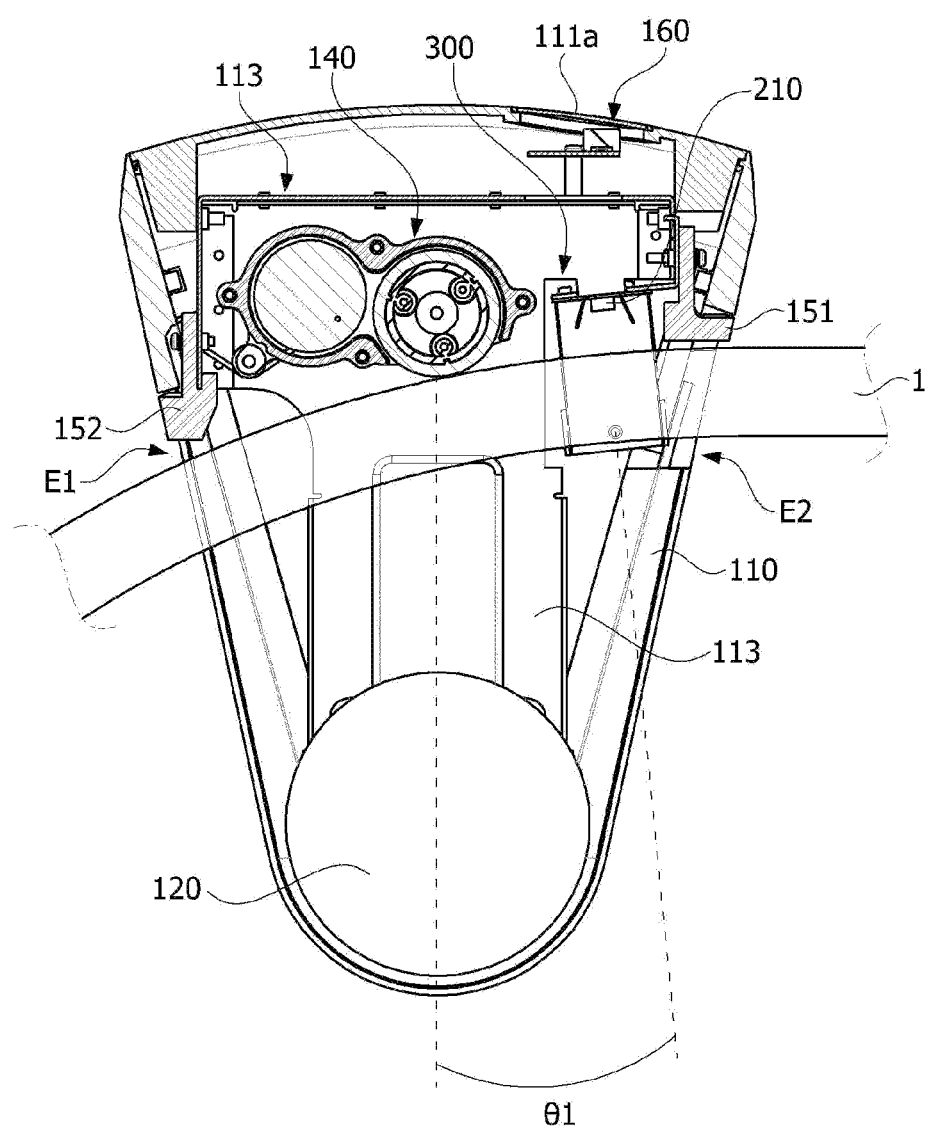

[FIG. 16]
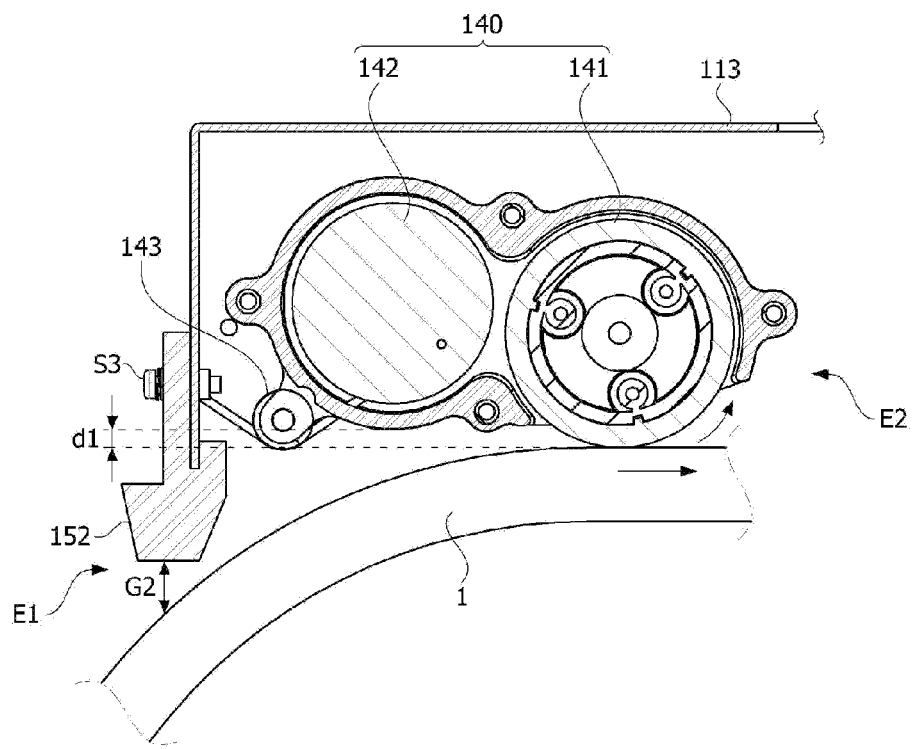
[FIG. 17]
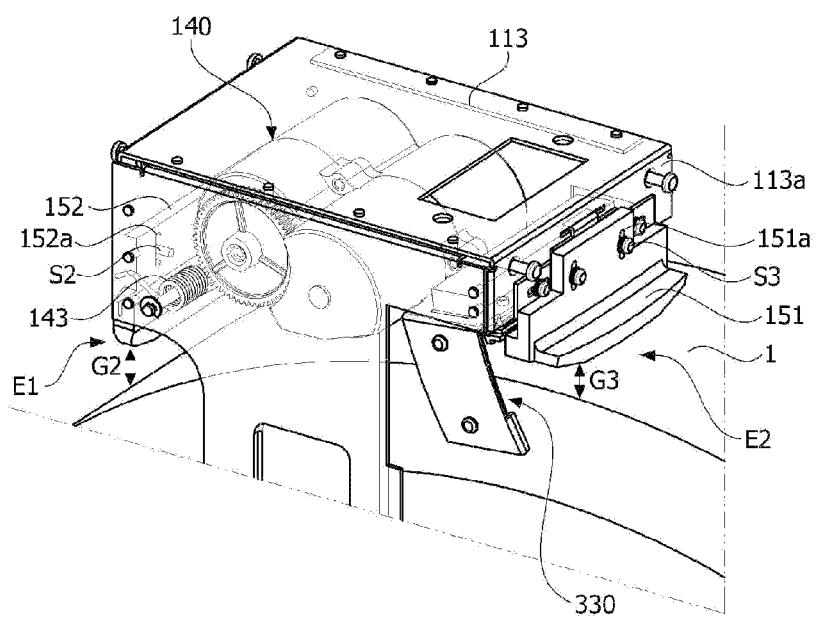

[FIG. 18]
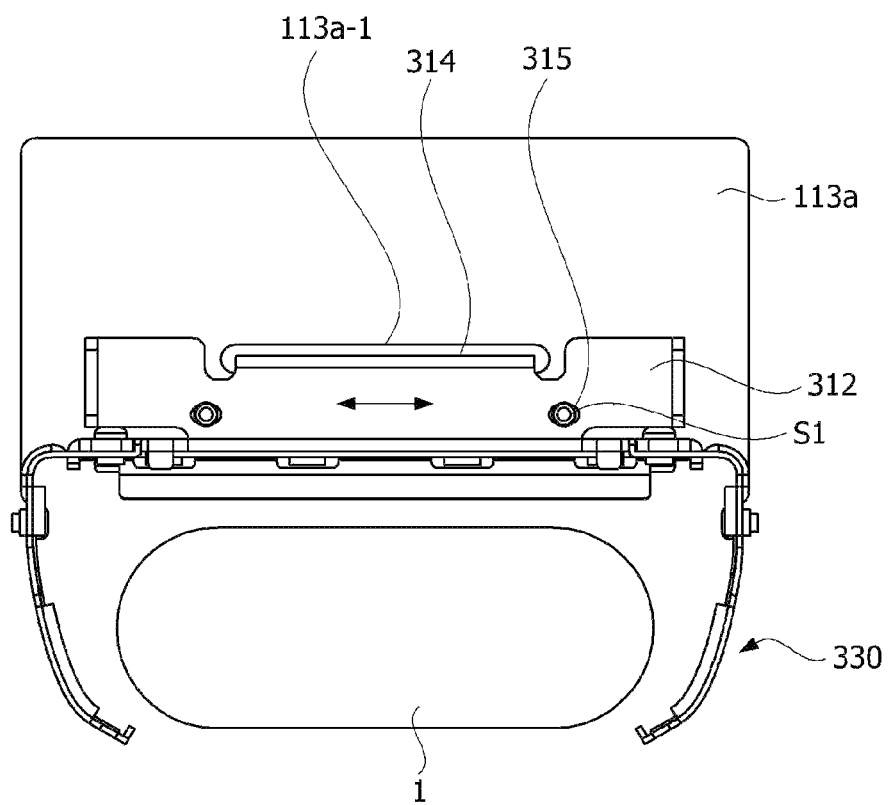

LIGHT SOURCE MODULE AND ULTRAVIOLET RAY IRRADIATING APPARATUS INCLUDING THE SAME

CROSS REFERENCE TO RELATED APPLICATIONS

This application is a Continuation of U.S. patent application Ser. No. 16/971,257 filed on Aug. 19, 2020 (now U.S. Pat. No. 11,305,028 issued on Apr. 19, 2022), which is the National Phase of PCT International Application No. PCT/KR2019/002059, filed on Feb. 20, 2019, which claims priority under 35 U.S.C. 119(a) to Patent Application No. 10-2018-0020050, filed in Republic of Korea on Feb. 20, 2018, all of which are hereby expressly incorporated by reference into the present application.

TECHNICAL FIELD

An embodiment relates to a light source module and an ultraviolet ray irradiating apparatus including the same.

BACKGROUND ART

An escalator and a moving walkway are installed in various places having a large floating population such as a subway station, an airport, a department store, and the like to be conveniently used by many people. However, a handrail which is a safety apparatus of the escalator or the moving walkway is easily exposed to bacteria.

Recently, an apparatus configured to sterilize a handrail using an ultraviolet light emitting element has been developed. The ultraviolet light emitting element can emit near ultraviolet wavelength light (UV-A), far ultraviolet wavelength light (UV-B), and deep ultraviolet wavelength light (UV-C). Among the above, the deep ultraviolet wavelength light (UV-C) can have a sterilizing function.

Since a user generally holds a handrail and moves, a side surface of the handrail can be easily exposed to bacteria. Accordingly, the side surface of the handrail has to be sterilized.

Further, the ultraviolet light emitting element can have an improved sterilization effect when uniformly emitting light to the handrail. However, since the handrail has various sizes and shapes, the sterilization effect is not guaranteed according to the type of mounted handrail.

SUMMARY

An embodiment is directed to providing a light source module capable of sterilizing even a side surface of a handrail and an ultraviolet ray irradiating apparatus including the same.

An embodiment is directed to providing a light source module capable of performing ultraviolet sterilization and thermal sterilization on the handrail at the same time.

An embodiment is directed to providing a light source module capable of adjusting a location thereof.

Problems desired to be solved by the present invention are not limited to the above-described problems, purposes and effects understood from solutions and embodiments which will be described below are also included.

One aspect of the present invention provides a light source module including: a fixing plate configured to extend in a first direction; a circuit board disposed on the fixing plate; a plurality of ultraviolet light emitting elements disposed on the circuit board in the first direction; a first reflection plate coupled to one side of the fixing plate; and a second reflection plate coupled to the other side of the fixing plate, wherein the first reflection plate and the second reflection plate include curved surfaces which become closer to each other as the distance from the circuit board increases, and the curved surface of the first reflection plate and the curved surface of the second reflection plate are disposed to be spaced apart in the first direction and disposed on a side surface of a target structure.

The light source module may include a first engaging member configured to fix the first reflection plate to the one side of the fixing plate and a second engaging member configured to fix the second reflection plate to the other side of the fixing plate.

The first reflection plate may include a first supporting plate fixed to one side of the fixing plate and a first reflection member disposed on one surface of the first supporting plate, the second reflection plate may include a second supporting plate fixed to the other side of the fixing plate and a second reflection member disposed on one surface of the second supporting plate, and one surface of the first supporting plate and one surface of the second supporting plate may be disposed to face each other.

A first direction distance between the first reflection member and the second reflection member may decrease as the distance from the circuit board increases.

The fixing plate may include a base portion to which the circuit board, the first reflection plate and the second reflection plate are fixed, a bent portion vertically bent from the base portion, and a protruding portion bent from the bent portion to be parallel with the base portion.

The light source module may include a third reflection plate and a fourth reflection plate disposed to be spaced apart from each other on the circuit board in a second direction perpendicular to the first direction, the third reflection plate and the fourth reflection plate may extend in the first direction, and a second direction distance between the third reflection plate and the fourth reflection plate may increase as the distance from the circuit board increases.

The light source module may include a fifth reflection plate disposed on the circuit board and configured to connect the third reflection plate and the fourth reflection plate, the fifth reflection plate may include a plurality of holes formed in the first direction, and the plurality of ultraviolet light emitting elements may be disposed in the plurality of holes.

Each of the curved surfaces of the first reflection plate and the second reflection plate may reflect some of light emitted from the plurality of ultraviolet light emitting elements to irradiate the side surface of the target structure with the light.

The target structure may be a handrail.

Another aspect of the present invention provides an ultraviolet ray irradiating apparatus including: a housing; a coupling part configured to fix the housing to a target structure; a light source module configured to irradiate the target structure with light; and a power module configured to supply power to the light source module, wherein the light source module includes a fixing plate configured to extend in a first direction, a circuit board disposed on the fixing plate, a plurality of ultraviolet light emitting elements disposed on the circuit board in the first direction, a first reflection plate coupled to one side of the fixing plate, and a second reflection plate coupled to the other side of the fixing plate, wherein the first reflection plate and the second reflection plate include curved surfaces which become closer to each other as a distance from the circuit board increases, and the curved surface of the first reflection plate and the curved surface of the second reflection plate are disposed to be spaced apart in the first direction and disposed on a side surface of a target structure.

The power module may rotate by movement of the target structure to generate power.

Each of the curved surfaces of the first reflection plate and the second reflection plate may reflect some of light emitted from the plurality of ultraviolet light emitting elements to irradiate a side surface of the target structure with the light.

The fixing plate may include a base portion to which the circuit board, the first reflection plate, and the second reflection plate are fixed, a bent portion disposed to be perpendicular to the base portion, and a protruding portion bent from the bent portion to be parallel with the base portion.

The protruding portion may be inserted into a guide hole disposed in the housing.

The light source module may include a first engaging member configured to fix the first reflection plate to the one side of the fixing plate, and a second engaging member configured to fix the second reflection plate to the other side of the fixing plate.

The first reflection plate may include a first supporting plate fixed to the one side of the fixing plate and a first reflection member disposed on one surface of the first supporting plate, the second reflection plate may include a second supporting plate fixed to the other side of the fixing plate and a second reflection member disposed on one surface of the second supporting plate, and the one surface of the first supporting plate and the one surface of the second supporting plate may face each other.

A first direction distance between the first reflection member and the second reflection member may decrease as the distance from the circuit board increases.

Advantageous Effects

According to an embodiment of the present invention, even a side surface of a handrail can be sterilized without providing a separate light source at the side surface.

Further, ultraviolet sterilization and thermal sterilization can be applied to the handrail at the same time to improve sterilizing power.

In addition, a sterilization effect can be improved by adjusting a location of a light source module.

Various useful advantages and effects of the present invention are not limited to the above and may be relatively easily understood in a process of describing exemplary embodiments of the present invention.

BRIEF DESCRIPTION OF THE DRAWINGS

FIG. 1 is a view illustrating a state in which an ultraviolet ray irradiating apparatus according to an embodiment of the present invention is mounted on a target structure.

FIG. 2 is a view for describing a process in which the target structure is sterilized by the ultraviolet ray irradiating apparatus according to the embodiment of the present invention.

FIG. 3A is a perspective view of a light source module in FIG. 2.

FIG. 3B is another perspective view of a light source module in FIG. 2.

FIG. 4 is an exploded view of FIG. 3.

FIG. 5 is a bottom view of the light source module.

FIG. 6 is a front view of the light source module.

FIG. 7 is a cross-sectional perspective view of the light source module.

FIG. 8 is a view for describing a process in which a handrail is sterilized by the light source module.

FIG. 9A is a first experimental example in which the reflection curvature of the light source module is adjusted.

FIG. 9B is a simulation result of an illuminance value of the first experimental example.

FIG. 10A is a second experimental example in which the reflection curvature of the light source module is adjusted.

FIG. 10B is a simulation result of an illuminance value of the second experimental example.

FIG. 11A is a third experimental example in which the reflection curvature of the light source module is adjusted.

FIG. 11B is a simulation result of an illuminance value of the third experimental example.

FIG. 12A is a fourth experimental example in which the reflection curvature of the light source module is adjusted.

FIG. 12B is a simulation result of an illuminance value of the fourth experimental example.

FIG. 13 is a view illustrating a state in which an ultraviolet ray irradiating apparatus according to another embodiment of the present invention is mounted on a target structure.

FIG. 14 is a perspective view of the ultraviolet ray irradiating apparatus according to another embodiment of the present invention.

FIG. 15 is a cross-sectional view of the ultraviolet ray irradiating apparatus according to another embodiment of the present invention.

FIG. 16 is a view illustrating a structure of a power module.

FIG. 17 is a view illustrating a state in which the light source module and the power module are mounted in a housing.

FIG. 18 is a view illustrating a state in which the light source module is mounted in the housing.

DETAILED DESCRIPTION

Embodiments of the present invention may be modified into other forms or some of the embodiments may be combined, and the scope of the present invention is not limited to embodiments which will be described below.

Although items described in a specific embodiment are not described in another embodiment, the items may be understood as a description related to the other embodiment unless a description opposite or contradictory to the items is in the other embodiment.

For example, when a characteristic of a configuration A is described in a specific embodiment and a characteristic of a configuration B is described in another embodiment, the characteristics of the configurations are understood to be in the scope of the present invention unless an opposite or contradictory description is present even when an embodiment in which the configuration A and the configuration B are combined is not clearly disclosed.

In the description of the embodiments, when one element is disclosed to be formed "on or under" another element, the term "on or under" includes both a case in which the two elements are in direct contact with each other and a case in which at least another element is disposed between the two elements (indirectly) to be formed. Further, when the term "on or under" is expressed, a meaning as an upward direction and a downward direction with respect to one element may also be included.

Hereinafter, embodiments of the present invention will be described in detail with reference to the accompanying drawings so that those skilled in the art may easily perform the embodiment of the present invention.

FIG. 1 is a view illustrating a state in which an ultraviolet ray irradiating apparatus according to an embodiment of the present invention is mounted on a target structure, and FIG. 2 is a view for describing a process in which the target structure is sterilized by the ultraviolet ray irradiating apparatus according to the embodiment of the present invention.

Referring to FIGS. 1 and 2, an ultraviolet ray irradiating apparatus 100 according to the embodiment of the present invention may be mounted on the target structure to sterilize a surface 1 of the target structure 2. The target structure 2 may include all various structures configured to move a user to a predetermined location such as an escalator or a moving walkway. The surface 1 of the target structure may be a handrail of the escalator or moving walkway but is not limited thereto. Hereinafter, the surface of the target structure is described as a handrail.

The ultraviolet ray irradiating apparatus 100 may include a light source module 300 disposed in a body 3 of the target structure 2 to irradiate the handrail 1 with light and a power part 11 configured to supply power to the light source module 300. In addition, the ultraviolet ray irradiating apparatus 100 may further include various components capable of checking a state of the target structure or detecting errors.

The ultraviolet ray irradiating apparatus 100 according to the embodiment may be mounted in the escalator or moving walkway to sterilize the handrail. Accordingly, the ultraviolet ray irradiating apparatus may not be seen from the outside. According to the structure, since an internal power source in the body may be used, a separate self-power generating device may be omitted.

The light source module 300 may sterilize the handrail 1 by irradiating ultraviolet light. An ultraviolet light emitting element 210 may emit near ultraviolet wavelength light (UV-A), far ultraviolet wavelength light (UV-B), and deep ultraviolet wavelength light (UV-C). A wavelength range may be determined by an Al composition ratio of a semiconductor structure.

For example, the near ultraviolet wavelength light (UV-A) may have a main peak wavelength in a range of 320 nm to 420 nm, the far ultraviolet wavelength light (UV-B) may have a main peak wavelength in a range of 280 nm to 320 nm, and the deep ultraviolet wavelength light (UV-C) may have a main peak wavelength in a range of 100 nm to 280 nm.

FIGS. 3A and 3B are perspective view of the light source module in FIG. 2, FIG. 4 is an exploded view of FIG. 3A, and FIG. 5 is a bottom view of the light source module.

Referring to FIGS. 3 to 5, the light source module 300 according to the embodiment may include a fixing plate 310 configured to extend in a first direction (an X-axis direction), a circuit board 340 disposed on the fixing plate 310, a plurality of ultraviolet light emitting elements 210 disposed on the circuit board 340 in the first direction, a first reflection plate 320 disposed at one side of the circuit board 340, and a second reflection plate 330 disposed at the other side of the circuit board 340.

The circuit board 340, the first reflection plate 320, and the second reflection plate 330 may be fixed to the fixing plate 310. A material of the fixing plate 310 is not particularly limited. For example, the fixing plate 310 may be made of an aluminum material.

The fixing plate 310 may include a base portion 311 to which the circuit board 340, the first reflection plate 320, and the second reflection plate 330 are fixed, a bent portion 312 disposed vertically from the base portion 311, and a protruding portion 314 disposed on the bent portion 312 to be parallel with the base portion 311. The base portion 311 may extend in the first direction and have one side and the other side.

The base portion 311 may include a lower surface on which the circuit board 340 is disposed and an upper surface facing the lower surface. The bent portion 312 may be vertically bent toward the upper surface of the base portion 311. Both end portions 313 of the bent portion 312 may be bent to face each other with respect to a center of the bent portion 312 in a horizontal direction. Accordingly, the user may easily adjust the bent portion 312 in a lateral direction by holding both end portions 313.

At least two holes 315 may be disposed in the bent portion 312. Screws may be engaged with the holes 315 to fix the light source module 300 to a desired location. Each of the holes 315 may extend in the first direction and have a predetermined width. Accordingly, the user may adjust the light source module 300 to the desired location after holding both end portions 313 in a state in which the screws are engaged with the holes 315.

The circuit board 340 may be mounted on the lower surface of the base portion 311. The circuit board 340 may extend in the first direction. The plurality of ultraviolet light emitting elements 210 may be disposed to be spaced apart on the circuit board 340 in the first direction. A spacing interval of the ultraviolet light emitting elements 210 may be appropriately adjusted so that the handrail can be irradiated with uniform light.

The first reflection plate 320 may be disposed at the one side of the circuit board 340. The first reflection plate 320 may include a first supporting plate 321 coupled to one side of the fixing plate 310 and a first reflection member 322 disposed on one surface of the first supporting plate 321. The first supporting plate 321 may include a first extending portion 323 configured to protrude toward the fixing plate 310.

Holes may be formed in the first extending portion 323. Accordingly, since a first engaging member 341 is coupled to the hole disposed in the base portion 311 and the hole of the first extending portion 323, the first reflection plate 320 may be fixed to the fixing plate 310. However, a method of fixing the first reflection plate 320 to the one side of the fixing plate 310 is not limited thereto. For example, the first reflection plate 320 and the fixing plate 310 may be coupled to each other by elastic coupling of a protrusion and a groove, and may be attached to each other by a separate adhesion.

The second reflection plate 330 may be coupled to the other side of the circuit board 340. The second reflection plate 330 may include a second supporting plate 331 coupled to the other side of the fixing plate 310 and a second reflection member 332 disposed on one surface of the second supporting plate 331. The one surface of the second supporting plate 331 may be disposed to face the one surface of the first supporting plate 321.

The second supporting plate 331 may include a second extending portion 333 configured to protrude toward the fixing plate 310. Holes may be formed in the second extending portion 333. Accordingly, since the first engaging member 341 is coupled to the hole disposed in the base portion 311 and the hole of the second extending portion 333, the first reflection plate 320 may be fixed to the fixing plate 310. However, a method of fixing the second reflection plate 330 to the one side of the fixing plate 310 is not limited thereto.

According to the embodiment in FIG. 3A, each of the first reflection plate 320 and the second reflection plate 330 may include curved surfaces C1 which approach each other as the distance from the circuit board 340 increases. According to the above, some of the light emitted from the ultraviolet light emitting element 210 is reflected from the curved surfaces to be irradiated to a side surface of the handrail without disposing a separate light source.

FIG. 3B is similar to FIG. 3A, but the first and second reflection plates 320 and 330 include inclined surfaces which approach each other as the distance from the circuit board 340 increases.

The first reflection member 322 and the second reflection member 332 may be fixed respectively to the first and second supporting plates 321 and 331 by second engaging members 342. However, the present invention is not limited to the above, and the first reflection member 322 and the second reflection member 332 may be respectively fixed to the first and second supporting plates 321 and 331 through various fixing methods (for example: elastic coupling method).

The first reflection member 322 and the second reflection member 332 may include a material having high reflectance with respect to ultraviolet light. For example, the first reflection member 322 and the second reflection member 332 may include aluminum but are not limited thereto.

The second reflection plate 330 may include a guide protrusion 331a to which the second reflection member 332 is inserted or fixed. The guide protrusion 331a may be disposed at an edge of the second reflection plate 330 to guide insertion of the second reflection member 332. Further, when the second reflection member 332 is fixed to the second reflection plate 330 by the second engaging member 342, the guide protrusion 331a may prevent the dislocation of the second reflection member 332 due to rotation of the second engaging member 342. The first reflection plate 320 may have the same shape as that of the second reflection plate 330. That is, the first reflection plate 320 may also include a guide protrusion 321a configured to fix the first reflection member 322.

According to the embodiment, since the curved surface C1 is formed in each of the first supporting plate 321 and the second supporting plate 331, each of the first reflection member 322 and the second reflection member 332 respectively coupled to the first supporting plate 321 and the second supporting plate 331 may also have a curved surface C1 having the same curvature. When the reflection plate is made of an aluminum material having a curved surface, although processing is difficult and manufacturing costs increase, according to the embodiment, processing becomes easy.

Referring to FIG. 6, the first reflection plate 320 may include an upper end portion F1 which is a straight section and a lower end portion F2 which is a curved section. The upper end portion F1 of the first reflection plate 320 is a bent portion connected to the fixing plate 310 and the lower end portion F2 of the first reflection plate 320 may be a bent curved surface to reflect the light emitted from the light emitting element 210 to the side surface. The second reflection plate 330 may also have an upper end portion F1 and a lower end portion F2.

A vertical length of the lower end portion F2 may be 1.5 to 2.5 times that of the upper end portion F1. When the length of the lower end portion F2 is smaller than 1.5 times the length of the upper end portion F1, the length of the lower end portion F2 is too small and thus it may be difficult for the light to be sufficiently irradiated to the side surface of the handrail, and when the length of the lower end portion F2 is greater than 2.5 times the length of the upper end portion F1, since the length of the lower end portion F2 is too large and thus an area which does not reflect the light to the side surface of the handrail increases, the size may unnecessarily increase.

The guide protrusion 321a of the first reflection plate 320 may include an upper guide protrusion 321a-1 disposed at the upper end portion F1 and a lower guide protrusion 321a-2 disposed at the lower end portion F2. The guide protrusion 331a of the second reflection plate 330 may also include an upper guide protrusion 331a-1 disposed at the upper end portion F1 and a lower guide protrusion 331a-2 disposed at the lower end portion F2. According to the above, separation of the first and second reflection members 322 and 333 from the first and second reflection plates 320 and 330 may be prevented.

A distance W1 between upper portions 322a and 332a of the first reflection member 322 and the second reflection member 332 may be greater than a distance W2 between lower portions 322b and 332b of the first reflection member 322 and the second reflection member 332. The upper portions 322a and 332a of the first reflection member 322 and the second reflection member 332 may be between the upper end portion F1 and the lower end portion F2 of the first reflection plate 320.

Referring to FIGS. 4 and 7, a reflection assembly 350 may be disposed at the circuit board 340 to uniformly control the light emitted from the ultraviolet light emitting elements 210. Accordingly, the efficiency of irradiating the ultraviolet light to an upper surface of the handrail may be improved.

The reflection assembly 350 may have a reflectance the same as that of a mirror by post-processing a front surface thereof. However, the present invention is not limited thereto and the reflection assembly 350 may be coated with aluminum.

The reflection assembly 350 may serve as a heat sink configured to discharge heat generated from the ultraviolet light emitting elements 210 to the outside. The light emitting element 210 according to the embodiment is an ultraviolet light emitting element and thus may generate relatively more heat in comparison with a visible light emitting element. Accordingly, it may be important to quickly discharge the heat. At this time, since the heat is discharged to the handrail, a function of sterilizing the handrail may also be performed.

The reflection assembly 350 may include a third reflection plate 351 and a fourth reflection plate 352 spaced apart from each other. The plurality of ultraviolet light emitting elements 210 may be disposed between the third reflection plate 351 and the fourth reflection plate 352.

According to the embodiment, an X-axis amount of the light emitted from the ultraviolet light emitting element 210 may be controlled by the first reflection plate 320 and the second reflection plate 330 and a Y-axis amount of the light may be controlled by the reflection assembly 350. That is, the first reflection plate 320 and the second reflection plate 330 may be disposed to be spaced apart from each other in the first direction (the X-axis direction) to control an X-axis light amount and the third reflection plate 351 and the fourth reflection plate 352 may be disposed to be spaced apart from each other in the second direction (the Y-axis direction) perpendicular to the first direction to control a Y-axis light amount.

The third reflection plate 351 and the fourth reflection plate 352 may be disposed to extend in the first direction and curved at a predetermined angle. Accordingly, a spacing distance between the third reflection plate 351 and the fourth reflection plate 352 may gradually increase as the distance from the circuit board 340 increases. For example, an angle formed by the third reflection plate 351 and the fourth reflection plate 352 may be 20 to 60° but is not necessarily limited thereto. That is, each of the first reflection plate 320 and the second reflection plate 330 may have a structure curved to become gradually closer to each other in a direction going away from the circuit board 340, whereas each of the third reflection plate 351 and the fourth reflection plate 352 may have a structure curved to be gradually more distant from each other in the direction going away from the circuit board 340.

The reflection assembly 350 is disposed at the circuit board 340 and may include a fifth reflection plate 353 configured to connect the third reflection plate 351 and the fourth reflection plate 352. The fifth reflection plate 353 may include a plurality of holes H1 disposed in the first direction. The plurality of light emitting elements 210 may be inserted into the plurality of holes H1, respectively.

The plurality of holes H1 may extend toward the third reflection plate 351 and the fourth reflection plate 352. Accordingly, side surfaces 210a of the plurality of ultraviolet light emitting elements 210 may be exposed to the outside of the reflection assembly 350. According to the structure, since the third reflection plate 351 and the fourth reflection plate 352 may be disposed closer to an upper surface of the light emitting element 210, a light amount may increase.

FIG. 8 is a view for describing a process in which the handrail is sterilized by the light source module.

Referring to FIG. 8, light L1 emitted from the plurality of ultraviolet light emitting elements 210 may be irradiated to the upper surface 1a of the handrail 1 to sterilize the handrail 1. In this case, heat H1 transferred to the reflection assembly 350 may be irradiated to the upper surface of the handrail 1. Accordingly, the reflection assembly 350 may quickly discharge the heat of the ultraviolet light emitting element 210, and may thermally sterilize or dry the handrail 1.

The first reflection plate 320 and the second reflection plate 330 may reflect light L2 emitted from the ultraviolet light emitting element 210 to irradiate the side surface of the handrail with the light L. The first reflection plate 320 and the second reflection plate 330 may have a curvature to reflect the light L2 emitted from the ultraviolet light emitting element 210. According to the configuration, the side surface 1b of the handrail 1 may be sterilized without disposing a separate light emitting element 210 at the side surface.

The first reflection plate 320 and the second reflection plate 330 may be disposed to surround the handrail 1. Accordingly, it may be difficult for the first reflection plate 320 and the second reflection plate 330 to be installed around the handrail 1 when fixed to the fixing plate 310. Particularly, when the distance (W2 in FIG. 6) between ends of the first reflection plate 320 and the second reflection plate 330 is smaller than a width of the handrail 1, it may be more difficult for the first reflection plate 320 and the second reflection plate 330 to be installed around the handrail 1 when fixed to the fixing plate 310.

However, the light source module 300 according to the embodiment may be easily installed because the first reflection plate 320 and the second reflection plate 330 may be coupled to the side surface of the fixing plate 310 after disposing the fixing plate 310 on the upper surface of the handrail 1 in advance. Particularly, the light source module 300 may be easily installed even when the distance (W2 in FIG. 6) between ends of the first reflection plate 320 and the second reflection plate 330 is smaller than the width of the handrail 1.

FIG. 9A is a first experimental example in which the reflection curvature of the light source module is adjusted, FIG. 9B is a simulation result of an illuminance value of the first experimental example, FIG. 10A is a second experimental example in which the reflection curvature of the light source module is adjusted, FIG. 10B is a simulation result of an illuminance value of the second experimental example, FIG. 11A is a third experimental example in which the reflection curvature of the light source module is adjusted, FIG. 11B is a simulation result of an illuminance value of the third experimental example, FIG. 12A is a fourth experimental example in which the reflection curvature of the light source module is adjusted, and FIG. 12B is a simulation result of an illuminance value of the fourth experimental example.

Referring to FIG. 9A, when a distance of a virtual line W3 which connects both end portions 332a and 332b of the curved surface of the reflection member in a straight line is 34 mm, and a distance W4 from the virtual line W3 to a maximum separation point 322c is 3 mm, a relative illuminance value was measured to be 0.0357 Dose. The maximum separation point 322c may be a point farthest away from the virtual line W3 in a vertical direction.

In FIG. 9B, a point at which an angle is 0° is the upper surface of the handrail and a point at which an angle increases from 0° to 180° is the side surface of the handrail. Further, a point at which an angle is 180° is a lower surface of the handrail. The light amount is greatest at the upper surface of the handrail and gradually decreases toward the side surface.

Referring to FIGS. 10A and 10B, when the distance W4 from the virtual line (W3, 34 mm) which connects both end portions 332a and 332b of the curved surface to the maximum separation point 322c is 5 mm, a relative illuminance value was measured to be 0.0517 Dose. That is, when a distance from the virtual line to a maximum curve is 5 mm, it is determined that ultraviolet illuminance is greatest and thus sterilizing power is greatest.

Referring to FIGS. 11A and 11B, when the distance W4 from the virtual line (W3, 34 mm) which connects both end portions 332a and 332b of the curved surface to the maximum separation point 322c is 7 mm, a relative illuminance value decreasing to 0.0371 Dose may be confirmed.

Further, referring to FIGS. 12A and 12B, when the distance W4 from the virtual line (W3, 34 mm) which connects both end portions of the curved surface to the maximum separation point 322c is 10 mm, a relative illuminance value was measured to be 0.0259 Dose. That is, when a curve excessively increases, a decrease in the relative illuminance value may be confirmed.

Referring to FIGS. 9 to 12, when the distance between the virtual line (34 mm) which connects both end portions 332a and 332b of the curved surface to the maximum separation point 322c is controlled to be smaller than 7 mm, or greater than or equal to 3 mm and smaller than 7 mm, greater sterilizing power may be secured. Accordingly, a ratio (W3:W4) between the virtual line W3 and the distance W4 from the virtual line to the maximum separation point 322c may be greater than or equal to 1:0.088 and smaller than 1:0.205.

In a vertical distance between both end portions 332a and 332b of the curved surface, a first distance L21 from the upper end portion 332a of the curved surface to the maximum separation point 322c may be greater than a second distance L22 from the maximum separation point 332c to the lower end portion 332b of the curved surface.

The first distance L21 may be 3.5 to 5 times the second distance L22. As shown in FIG. 9, when the first distance L21 is smaller than 3.5 times the second distance L22, since the second distance L22 becomes relatively large and thus the curvature decreases, it may be difficult for the light to be reflected to the side surface of the handrail. Further, when the first distance L21 is greater than 5 times the second distance L22, since the second distance becomes too small, it is difficult to secure an area for reflecting the light to the side surface of the handrail.

FIG. 13 is a view illustrating a state in which an ultraviolet ray irradiating apparatus according to another embodiment of the present invention is mounted on a target structure and FIG. 14 is a perspective view of the ultraviolet ray irradiating apparatus according to another embodiment of the present invention.

The ultraviolet ray irradiating apparatus 100 according to the embodiment of the present invention may be mounted on the target structure to sterilize a surface of the target structure. In this case, the ultraviolet ray irradiating apparatus 100 may be mounted at the outside rather than disposed in the target structure as described above.

The ultraviolet ray irradiating apparatus 100 may include a front case 111 in which a window 111a configured to output information related to sterilization is disposed and a side case 112 configured to extend from the front case 111 and mounted on the target structure. The side case 112 may have a triangular shape having a decreasing width when becoming more distant from the front case but is not necessarily limited thereto.

FIG. 15 is a cross-sectional view of the ultraviolet ray irradiating apparatus according to another embodiment of the present invention and FIG. 16 is a view illustrating a structure of a power module.

Referring to FIG. 15, the ultraviolet ray irradiating apparatus according to the embodiment may include a coupling part 120 configured to fix a housing 113 to the target structure, a light source module 300 configured to irradiate the handrail 1 with ultraviolet light, and a power module 140 configured to supply power to the light source module 300. The light source module 300 may be disposed to be curved at a predetermined angle θ1 from a vertical direction of the housing 113. All the above-described structures may be applied to the light source module 300. The light source module 300 according to the embodiment may be applied to both an embedded structure as shown in FIG. 1 and an external structure as shown in FIG. 15.

The housing 113 may accommodate the light source module 300 and the power module 140. The shape or material of the housing 113 is not particularly limited. A display part 160 configured to display a state of a present light source device may be disposed at an upper part of the housing 113. The display part 160 may include a separate liquid crystal panel or light emitting diodes having various colors capable of displaying a state.

The housing 113 may include an inlet E1 and an outlet E2 through which the handrail 1 of the target structure passes. The handrail 1 may continuously pass through the inside of the housing 113 through the inlet E1 and the outlet E2.

A first brush 152 may be disposed at the inlet E1 of the housing 113 to prevent introduction of a user's hand or foreign matter into the light source device and a second brush 151 may be disposed at the outlet E2 of the housing 113 to prevent the introduction of a user's hand or foreign matter into the light source device.

The power module 140 may rotate with the handrail 1 to generate electric power. The generated electric power may drive the ultraviolet light emitting elements 210 of the light source module 300.

Referring to FIG. 16, the power module 140 may include a roller 141 configured to come into contact with the handrail 1 and a power supply part 142 rotated by the roller 141 to generate electric power. The roller 141 and the power supply part 142 may be connected by a gear (not shown). The power module 140 may include all of various self-power generating structures capable of converting a rotating force of the roller 141 into electric power.

The power module 140 may directly provide the electric power generated from the power supply part 142 to the light source module 300 but is not necessarily limited thereto. For example, the power module 140 may store some of the generated electric power in a battery (not shown). Accordingly, the electric power stored in the battery may be used when necessary.

The roller 141 and the power supply part 142 may be disposed in a direction from the inlet E1 to the outlet E2 and the roller 141 may be disposed farther away from the inlet E1 in comparison with the power supply part 142. That is, the roller 141 may be disposed closer to the light source module 300 in comparison with the power supply part 142. According to the configuration, a problem in which a user's hand is inserted into the light source device by the roller 141 may be prevented by disposing the roller 141 relatively far away.

The power module 140 may include an elastic member 143 connected to the housing 113. The elastic member 143 may connect the power module 140 to the inlet E1 side of the housing 113. The elastic member 143 may have an elastic force so that the roller 141 may come into contact with the handrail 1. Accordingly, the elastic member 143 may allow the roller 141 to come into close contact with the upper surface of the handrail 1. According to the embodiment, a location of the power supply part 142 may be disposed a predetermined distance d1 higher than a location at which the roller 141 comes into contact with the handrail 1 to be spaced apart from the handrail 1.

FIG. 17 is a view illustrating a state in which the light source module and the power module are mounted in the housing, and FIG. 18 is a view illustrating a state in which the light source module is mounted in the housing.

The light source module 300 may irradiate the handrail 1 with the ultraviolet light to sterilize a surface of the handrail 1. The light source module 300 may irradiate a three-dimensional surface (Topology) of the target structure with the light. When the irradiated light is an ultraviolet ray, the surface of the handrail 1 may be sterilized.

As described above, the light source module 300 may sterilize even a side surface of the handrail due to the reflection plate 330. Generally, the user holds the handrail 1 and thus comes into contact with not only the upper surface of the handrail 1 but also the side surface of the handrail 1. Accordingly, when the side surface of the handrail 1 is also sterilized, a sterilization effect may be further improved.

In this case, when each of the ultraviolet light emitting elements uniformly irradiates an area of the handrail 1 with the light, the sterilization effect may be improved. However, since the handrail 1 has various shapes and sizes, a location of the light source module 300 is necessary to be adjusted according to the type of the handrail 1.

The light source module 300 may include a location adjusting part configured to adjust a location where the bent portion 312 is fixed to the housing 113. The location adjusting part may include at least one hole 315 and a first screw S1.

The hole 315 may extend in the first direction (the X-axis direction) which is a longitudinal direction of the circuit board. Accordingly, since the first screw S1 is coupled to the light source module 300 after moving the light source module 300 to a desired location along the longitudinal direction of the circuit board, the location where the module 300 is fixed to the housing 113 may be adjusted.

In this case, since the protruding portion 314 is inserted into a guide hole 113a-1 of the housing 113, the light source module 300 may be mounted on a front surface portion 113a of the housing before coupling the first screw S1 to the hole 315. Accordingly, the location for mounting the light source module 300 may be easily and accurately adjusted.

While the embodiments of the inventive concept have been described with reference to the accompanying drawings, it should be understood by those skilled in the art that various modifications may be made without departing from the scope of the inventive concept and without changing essential features thereof.

What is claimed is:

1. A light source module comprising:
   a fixing plate configured to extend in a first direction;
   a circuit board disposed on the fixing plate;
   a plurality of ultraviolet light emitting elements disposed on the circuit board in the first direction;
   a first reflection plate disposed at one side of the fixing plate; and
   a second reflection plate disposed at the other side of the fixing plate,
   wherein the plurality of ultraviolet light emitting elements are disposed between the first reflection plate and the second reflection plate in the first direction.

2. The light source module of claim 1, wherein the first reflection plate and the second reflection plate comprise inclined surfaces which become closer to each other as a distance from the circuit board increases.

3. The light source module of claim 2, wherein
   the first reflection plate comprises a first supporting plate coupled to the one side of the fixing plate and a first reflection member disposed on one surface of the first supporting plate; and
   the second reflection plate comprises a second supporting plate coupled to the other side of the fixing plate and a second reflection member disposed on one surface of the second supporting plate.

4. The light source module of claim 3, wherein the first supporting plate comprises a first extending portion protruded toward the fixing plate, and the second supporting plate comprises a second extending portion protruded toward the fixing plate.

5. The light source module of claim 3, wherein
   the first reflection plate comprises a first guide protrusion to which the first reflection plate is inserted or fixed, and
   the second reflection plate comprises a second guide protrusion to which the second reflection member is inserted or fixed.

6. The light source module of claim 1, wherein
   each of the first reflection plate and the second reflection plate comprises a straight upper end portion and a curved lower end portion, and
   wherein the upper end portion is connected to the fixing plate through a bent portion.

7. The light source module of claim 6, wherein a vertical length of the lower end portion is 1.5 to 2.5 times that of the upper end portion.

8. The light source module of claim 1, further comprising:
   a reflection assembly is disposed at the circuit board.

9. The light source module of claim 8, wherein the reflection assembly comprises a third reflection plate and a fourth reflection plate disposed to be spaced apart from each other on the circuit board in a second direction perpendicular to the first direction, and
   wherein the plurality of ultraviolet light emitting elements are disposed between the third reflection plate and the fourth reflection plate in the second direction.

10. The light source module of claim 9, wherein the reflection assembly comprises a fifth reflection plate configured to connect the third reflection plate and the fourth reflection plate,
    wherein the fifth reflection plate comprises a plurality of holes formed in the first direction, and
    wherein the plurality of ultraviolet light emitting elements are disposed in the plurality of holes, respectively.

11. An ultraviolet ray irradiating apparatus comprising:
    a light source module configured to irradiate a target structure with light, and comprises a fixing plate configured to extend in a first direction, a circuit board disposed on the fixing plate, a plurality of ultraviolet light emitting elements disposed on the circuit board in the first direction, a first reflection plate disposed at one side of the fixing plate, and a second reflection plate disposed at the other side of the fixing plate, wherein the plurality of ultraviolet light emitting elements are disposed between the first reflection plate and the second reflection plate in the first direction, and
    a power module configured to supply power to the light source module.

12. The ultraviolet ray irradiating apparatus of claim 11, wherein the first reflection plate and the second reflection plate comprise inclined surfaces which become closer to each other as a distance from the circuit board increases.

13. The ultraviolet ray irradiating apparatus of claim 11, further comprising:
    a housing configured to accommodate the light source module and the power module and comprises an inlet and an outlet through which the target structure passes.

14. The ultraviolet ray irradiating apparatus of claim 13, further comprising:
    a coupling part configured to fix the housing to a target structure.

15. The ultraviolet ray irradiating apparatus of claim 14, wherein the target structure is a handrail.

16. The ultraviolet ray irradiating apparatus of claim 13, wherein the power module rotates by movement of the target structure to generate power.

17. The ultraviolet ray irradiating apparatus of claim 16, wherein the power module comprises a roller configured to come into contact with the target structure and a power supply part rotated by the roller to generate electric power.

18. The ultraviolet ray irradiating apparatus of claim 17, wherein the roller and the power supply part are disposed in a direction from the inlet to the outlet of the housing.

19. The ultraviolet ray irradiating apparatus of claim 13, wherein the power module comprises an elastic member connected to the housing and configured to connect the power module to the inlet of the housing.

20. The ultraviolet ray irradiating apparatus of claim 13, wherein the light source module further comprises a location adjusting part configured to adjust a location where a bent portion of the fixing plate is fixed to the housing.

* * * * *